United States Patent
Seebaluck et al.

(10) Patent No.: US 12,345,691 B2
(45) Date of Patent: Jul. 1, 2025

(54) DUST PARTICULATE SEPARATOR FOR DUCTED SMOKE DETECTORS

(71) Applicant: Kidde Technologies Inc., Wilson, NC (US)

(72) Inventors: Len D. Seebaluck, Wake Forest, NC (US); Aaron S. Rogers, Surf City, NC (US)

(73) Assignee: Kidde Technologies, Inc., Wilson, NC (US)

( * ) Notice: Subject to any disclaimer, the term of this patent is extended or adjusted under 35 U.S.C. 154(b) by 288 days.

(21) Appl. No.: 18/198,450

(22) Filed: May 17, 2023

(65) Prior Publication Data

US 2024/0385160 A1 Nov. 21, 2024

(51) Int. Cl.
*G01N 1/10* (2006.01)
*G01N 33/00* (2006.01)

(52) U.S. Cl.
CPC .................. *G01N 33/0011* (2013.01)

(58) Field of Classification Search
CPC .................................................. G01N 1/2202
See application file for complete search history.

(56) References Cited

U.S. PATENT DOCUMENTS

| | | | |
|---|---|---|---|
| 3,930,802 A * | 1/1976 | Beasley | F23G 7/065 110/211 |
| 4,245,396 A | 1/1981 | Maffet | |
| 6,936,095 B2 * | 8/2005 | North | B04C 5/15 96/403 |
| 7,669,457 B2 | 3/2010 | Griffith et al. | |
| 2001/0035462 A1 * | 11/2001 | Collazo | F24F 11/0001 236/49.2 |
| 2012/0031200 A1 | 2/2012 | Ito | |

FOREIGN PATENT DOCUMENTS

| | | |
|---|---|---|
| CN | 104749004 A | 7/2015 |
| EP | 2320398 A1 | 5/2011 |
| EP | 3494560 B1 | 6/2020 |
| WO | 0203845 A1 | 1/2002 |
| WO | 2013182822 A1 | 12/2013 |

OTHER PUBLICATIONS

Extended European Search Report for EP Application No. 24176654. 2, dated Oct. 18, 2024, 9 pages.

* cited by examiner

*Primary Examiner* — John E Breene
*Assistant Examiner* — Alex T Devito
(74) *Attorney, Agent, or Firm* — Kinney & Lange, P.A.

(57) ABSTRACT

A ducted smoke detector includes a housing defining an interior cavity, an air inlet in fluid communication with the interior cavity, an air outlet in fluid communication with the interior cavity, a smoke sensing chamber disposed in the interior cavity, and a particulate separator disposed between and in fluid communication with the air inlet and the smoke sensing chamber in the interior cavity. The particulate separator includes a shaft, a perforated wall disposed around the shaft, and a plurality of deflection vanes disposed on the shaft. The perforated wall extends from a first open end to a second open end, is connected to the shaft, and is configured to rotate with the shaft. The plurality of deflection vanes is disposed on the shaft and extend radially outward toward the perforated wall, the plurality of deflection vanes configured to rotate with the shaft and the perforated wall.

20 Claims, 6 Drawing Sheets

DUST PARTICULATE SEPARATOR FOR DUCTED SMOKE DETECTORS

BACKGROUND

The present disclosure is directed generally to smoke detectors and more particularly to ducted smoke detectors for use in an aircraft.

Ducted smoke detectors are utilized on modern commercial aircraft to protect avionics bays of electronic controllers as well as air conditioner pack HEPA filters from thermal combustion. Ducted smoke detectors typically include a photo-electric smoke detector housed in a sealed enclosure with an inlet and exhaust duct port. The smoke detectors are disposed in an air return path that picks up dust particulates that can plug the ducted smoke detector, causing the smoke detector to become inoperable. Unscheduled maintenance is often required to remove and clean the smoke detector.

New technologies are needed to remove dust particulates from ducted smoke detectors to improve reliability of the smoke detector and reduce maintenance requirements.

SUMMARY

A ducted smoke detector includes a housing defining an interior cavity, an air inlet in fluid communication with the interior cavity, an air outlet in fluid communication with the interior cavity, a smoke sensing chamber disposed in the interior cavity, and a particulate separator disposed between and in fluid communication with the air inlet and the smoke sensing chamber in the interior cavity. The particulate separator includes a shaft, a perforated wall disposed around the shaft, and a plurality of deflection vanes disposed on the shaft. The perforated wall extends from a first open end to a second open end, is connected to the shaft, and is configured to rotate with the shaft. The plurality of deflection vanes is disposed on the shaft and extend radially outward toward the perforated wall, the plurality of deflection vanes configured to rotate with the shaft and the perforated wall.

The present summary is provided only by way of example, and not limitation. Other aspects of the present disclosure will be appreciated in view of the entirety of the present disclosure, including the entire text, claims and accompanying figures.

Figure 1:
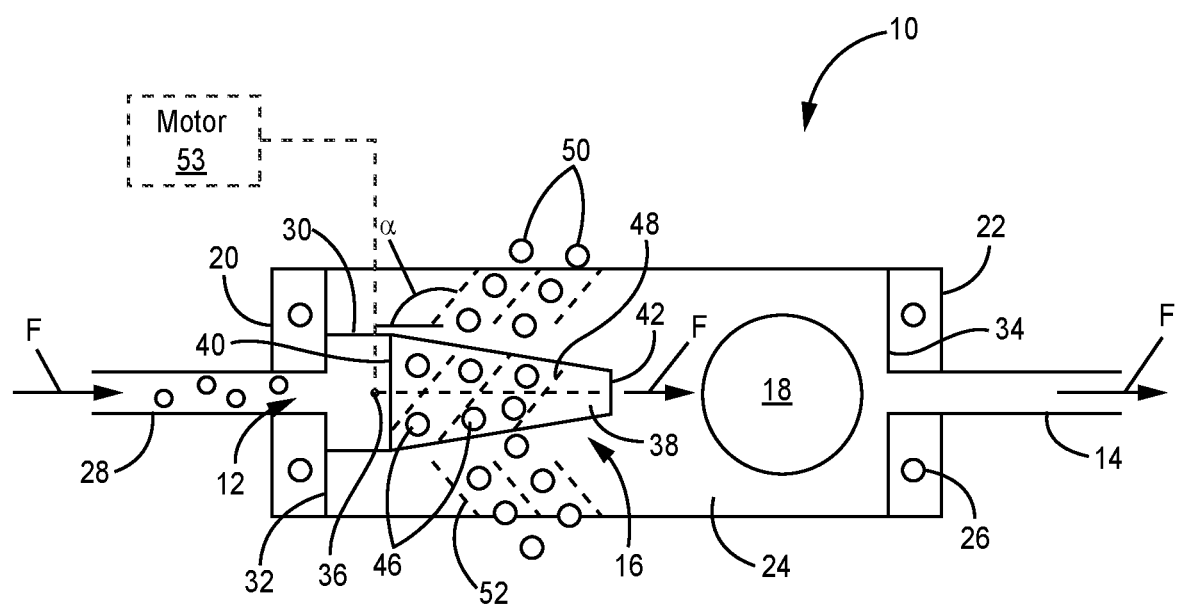
FIG. 1 is a schematic top view of an internal cavity of a ducted smoke detector having a dust particulate separator.

While the above-identified figures set forth embodiments of the present invention, other embodiments are also contemplated, as noted in the discussion. In all cases, this disclosure presents the invention by way of representation and not limitation. It should be understood that numerous other modifications and embodiments can be devised by those skilled in the art, which fall within the scope and spirit of the principles of the invention. The figures may not be drawn to scale, and applications and embodiments of the present invention may include features, steps and/or components not specifically shown in the drawings.

DETAILED DESCRIPTION

The present disclosure is directed to a ducted smoke detector for an aircraft. The ducted smoke detector includes a dust particulate separator at an air inlet to collect and disperse dust particulates outside a smoke detector chamber to prevent clogging of the smoke detector chamber. The disclosed dust particulate separator and associated features described herein can improve operability and reduce maintenance requirements of the ducted smoke detector. The disclosed dust particulate separator can minimize or eliminate the need for unscheduled smoke detector cleaning maintenance and allow the aircraft to maintain a higher level of operational readiness.

FIG. 1 is a schematic top view of an internal cavity of ducted smoke detector 10. Air inlet 12, air outlet 14, particulate separator 16, smoke sensing chamber 18, first end 20, second end 22, base plate 24, mounting holes 26, inlet conduit 28, inlet expander 30, first housing end wall 32, second housing end wall 34, shaft 36, perforated wall 38, inlet end 40, outlet end 42, holes 46, deflection vanes 48 (shown in phantom), particulates 50, ribs 52 (shown in phantom), motor 53, and airflow F are shown. Top walls of a housing are removed to show components of the internal cavity.

Ducted smoke detector 10 is configured for use in an aircraft to protect avionics bays of electronic controllers as well as air conditioner pack HEPA filters from thermal combustion. Ducted smoke detector 10 is a flow-through smoke detector configured to be disposed in an air conditioning air return path. A portion of the return air can be drawn through ducted smoke detector 10 from air inlet 12 to air outlet 14. Air inlet 12 is configured to receive a portion of the return air (airflow F), which includes particulates 50 (dust and other larger particles capable of clogging smoke sensing chamber 18). Air outlet 14 can be coupled to the air conditioning system. Particulate separator 16, in combination with additional features described herein, is configured to purge particulates 50 from airflow F received from air inlet 12, such that the amount of particulates 50 reaching smoke sensing chamber 18 is significantly reduced.

Ducted smoke detector 10 extends longitudinally from first end 20 to second end 22. Air inlet 12 is disposed at first end 20. Air outlet 14 is disposed at second end 22. Air inlet 12 extends through first housing end wall 32. Air outlet 14 extends through second housing end wall 34. Air inlet 12 can be longitudinally aligned with air outlet 14. Particulate separator 16 is disposed adjacent to air inlet 12. Inlet end 40 of particulate separator 16 is disposed adjacent air inlet 12. Outlet end 42 of particulate separator 16 faces smoke sensing chamber 18. Smoke sensing chamber 18 is disposed between particulate separator 16 and air outlet 14. Particulate separator 16 and smoke sensing chamber 18 can be aligned longitudinally with air inlet 12 and air outlet 14. Smoke sensing chamber 18 is disposed on base plate 24. Base plate 24 includes mounting holes 26 configured for mounting ducted smoke detector 10 to a surface. Base plate 24 additionally includes electronics (shown in FIGS. 2 and 3) for operation of ducted smoke detector 10.

Air inlet 12 can include inlet conduit 28 and inlet expander 30. Inlet conduit 28 extends outward from the internal cavity of ducted smoke detector 10 and is in fluid communication with the internal cavity. Inlet conduit 28 is configured to direct airflow F into the internal cavity of ducted smoke detector 10. Inlet expander 30 is disposed in the internal cavity at an end of inlet conduit 28. Inlet expander 30 extends from first housing end wall 32 toward inlet end 40 of particulate separator 16. Inlet expander 30 is cylindrical having a diameter substantially matching a diameter of particulate separator 16 at inlet end 40. Inlet expander 30 is aligned with inlet end 40. Inlet expander 30 is configured to direct airflow F to particulate separator 16. Inlet expander 30 is spaced from particulate separator 16 at inlet end 40 to allow rotation of particulate separator 16. In alternative embodiments, air inlet 12 can have a uniform diameter matching a diameter of inlet end 40 of particulate separator 16. Inlet end 40 of particulate separator 16 can be disposed adjacent to first housing end wall 32. Air inlet 12 can have any configuration suitable for directing airflow F entering ducted smoke detector 10 into particulate separator 16 and preventing or limiting airflow F entering ducted smoke detector 10 from bypassing particulate separator 16.

Particulate separator 16 includes perforated wall 38, inlet end 40, outlet end 42, shaft 36, holes 46, and deflection vanes 48. Particulate separator 16 has a frustoconical shape defined by perforated wall 38 extending from and decreasing in diameter from inlet end 40 to outlet end 42. Inlet end 40 and outlet end 42 are open to airflow F. Perforated wall 38 is disposed around shaft 36 and configured to rotate with shaft 36. Perforated wall 38 can be connected to shaft 36 by struts (shown in FIG. 6) and/or deflection vanes 48. Struts can extend from perforated wall 38 to shaft 36, for example, at inlet end 40 and outlet end 42. Deflection vanes 48 can extend radially outward from shaft 36 toward perforated wall 38. Deflection vanes 48 can be disposed at varying locations along a length of shaft 36 and perforated wall 38. As used herein, the term "deflection vanes" can refer to a single vane body with multiple revolutions around shaft 36, multiple vane bodies, or multiple vanes disposed at varying locations around shaft 36. Deflection vanes 48 can be configured to cause rotation of particulate separator 16 when airflow F is received in particulate separator 16 from air inlet 12. In some embodiments, rotation of particulate separator 16 can be additionally and/or alternatively driven by a motor 53, as described further herein. As discussed further herein, shaft 36 is rotatably mounted to a housing of ducted smoke detector 10. Optional motor 53 can be connected to shaft 36, for example at inlet end 40 as shown.

Perforated wall 38 includes a plurality of holes 46 of varying size. Hole size decreases along perforated wall 38 from inlet end 40 to outlet end 42. Holes 46 disposed adjacent to inlet end 40 have a larger diameter than holes 46 disposed adjacent to outlet end 42. Hole size can be selected to accommodate passage of dust particulates 50, which can generally range from 1 to 10 microns. Holes 46 are disposed around a circumference of perforated wall 38. In some embodiments, holes 46 can be provided in rings. In other embodiments, holes 46 can be provided with non-uniform or irregular spacing. Holes 46 are configured to expel particulates 50 collected in particulate separator 16. As particulate separator 16 rotates, particulates 50 are forced outward toward perforated wall 38 by centrifugal force. An air vortex is formed inside particulate separator 16, which separates particulates 50 from airflow F and forces particulates 50 toward perforated wall 38 where they can be expelled through holes 46. Heavier and larger particulates 50 are forced outward first and can be expelled through larger holes 46 disposed at an upstream end of particulate separator 16 adjacent to inlet end 40. Lighter and smaller particles are expelled through smaller holes 46 in a downstream portion of particulate separator 16 adjacent to outlet end 42. The number, size, and location of holes 46 can be selected to provide a desired reduction in particulates 50 in airflow F at outlet end 42. Smoke particles are approximately $\frac{1}{10}^{th}$ the size of dust particulates 50 and can remain entrained in airflow F at the center of particulate separator 16. Smoke particles can exit particulate separator at outlet end 42.

Perforated wall 38 can be formed of any suitable lightweight material, including but not limited to aluminum. Perforated wall 38 can be formed, for example, from sheet metal. Holes 46 can be formed, for example, by drilling. In some embodiments, particulate separator 16 can have a length of approximately 3 inches (approximately 7.62 cm) with a 1-inch diameter (approximately 2.54 cm) opening at inlet end 40 and a 0.5-inch (approximately 1.27 cm) diameter opening at outlet end 42.

Particulates 50 expelled through perforated wall 38 can be expelled from ducted smoke detector 10 through vent louvers (shown in FIGS. 2-4) in a housing of ducted smoke detector 10, as described further herein. Particulates 50 expelled through vent louvers can be guided away from air inlet 12 by ribs 52 (shown in phantom) disposed on an external surface of the housing. Ribs 52 can be arranged to guide a flow of particulates 50 away from air inlet 12 to prevent particulates 50 from entering air inlet 12. For example, ribs 52 can be angled from particulate separator 16 away from air inlet 12 such that ribs 52 are disposed at an obtuse angle α relative to air inlet 12.

Outlet end 42 of particulate separator 16 is disposed upstream of smoke sensing chamber 18. Outlet end 42 can be spaced from smoke sensing chamber 18 to direct airflow F toward an upstream face of smoke sensor chamber 18. Ducting or housing can be configured to direct airflow F from outlet end 42 of particulate separator 16 toward smoke sensing chamber 18.

Smoke sensing chamber 18 receives airflow F from particulate separator 16. Smoke sensing chamber 18 is configured to detect smoke particles using technology known in the art. Smoke sensing chamber 18 includes a perforated screen (not shown) to prevent dust particulates 50 from entering smoke sensing chamber 18. Smoke sensors are capable of optical discrimination to distinguish smoke particles from dust particulates 50 that enter smoke sensing chamber 18. Smoke sensing chamber 18 is disposed on base plate 24. Smoke sensing chamber 18 is disposed adjacent to air outlet 14.

Ducted smoke detector 10 can be configured to detect airflow F through ducted smoke detector 10 and/or rotation of particulate separator 16. Ducted smoke detector 10 and/or controller device in communication with components of ducted smoke detector 10 can be configured to trigger an alarm if airflow F is insufficient to drive particulate separator 16 and/or if rotation of particulate separator 16 has ceased. Ducted smoke detector can include one or more sensors (not shown) configured to detect airflow F and/or sense rotation of particulate separator 16. For example, airflow F through ducted smoke detector 10 can be detected and measured by a solid-state air flow sensor or other airflow sensing device known in the art. In other examples, airflow F can be determined based on a pressure differential between inlet end 40 and outlet end 42 using pressure sensors. In some examples, an optical encoder or other optical sensor can be used to detect rotation of particulate separator 16. For example, a device can be configured to detect a beam of light emitted through particulate separator 16, in a direction perpendicular to the axis of rotation, through aligned holes 46 disposed on opposite sides of perforated wall 38. Intermittent or oscillating detection of the light beam will indicate rotation of particulate separator 16 as solid portions of perforated wall 38 intermittently interrupts transmission. No detection or constant detection will indicate rotation has ceased. A slowing rate of detection can indicate rotation has slowed. In other examples, an element disposed directly on shaft 36 or perforated wall 38 can be used to interrupt a beam of light. Other means for detecting airflow F and/or rotation of particulate separator 16 are contemplated. In some embodiments, an alarm indicating insufficient airflow F or rotation of particulate separator 16, detected by one or more sensors, can trigger operation of motor 53 to drive particulate separator 16.

Figure 2:
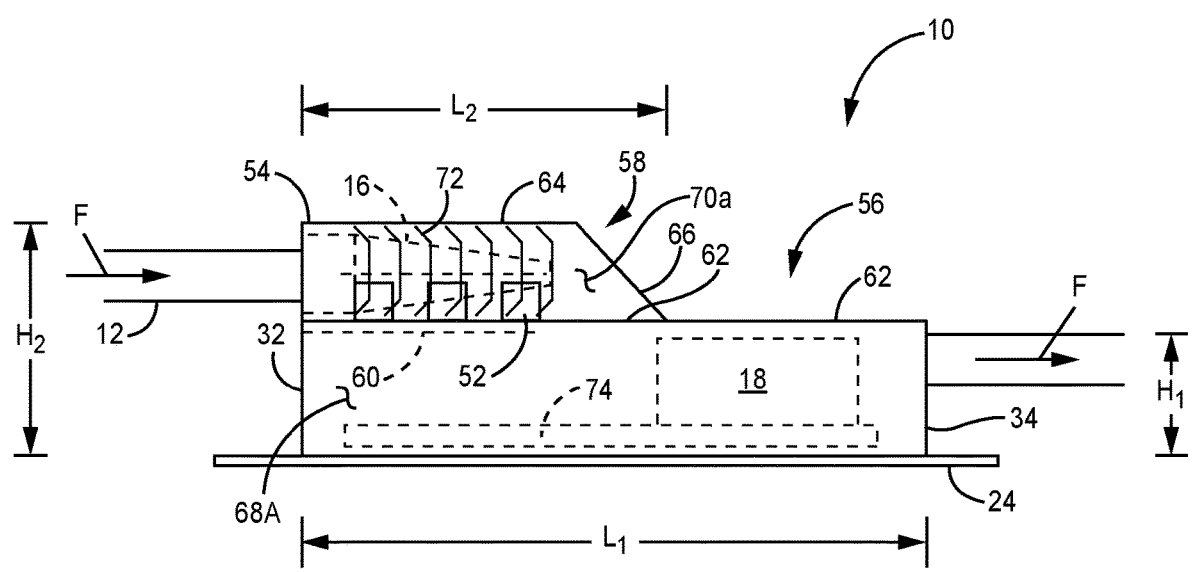
FIG. 2 is a schematic side view of the ducted smoke detector.
Figure 3:
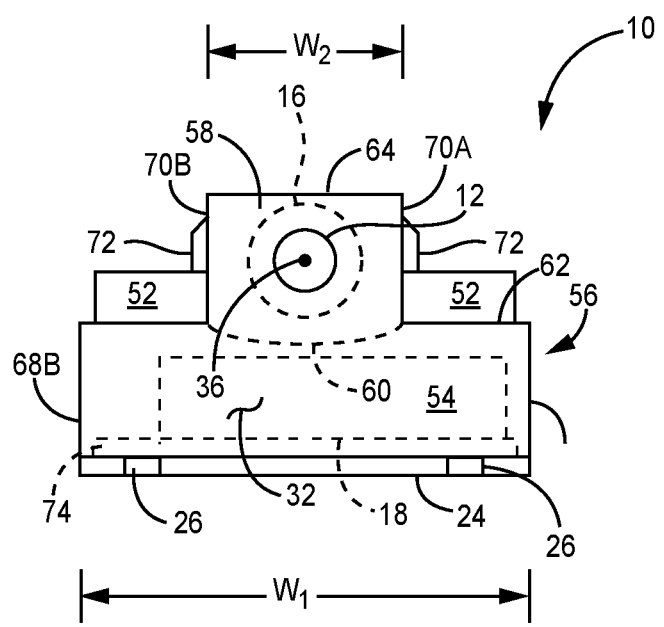
FIG. 3 is a schematic front view of the ducted smoke detector.
Figure 4:
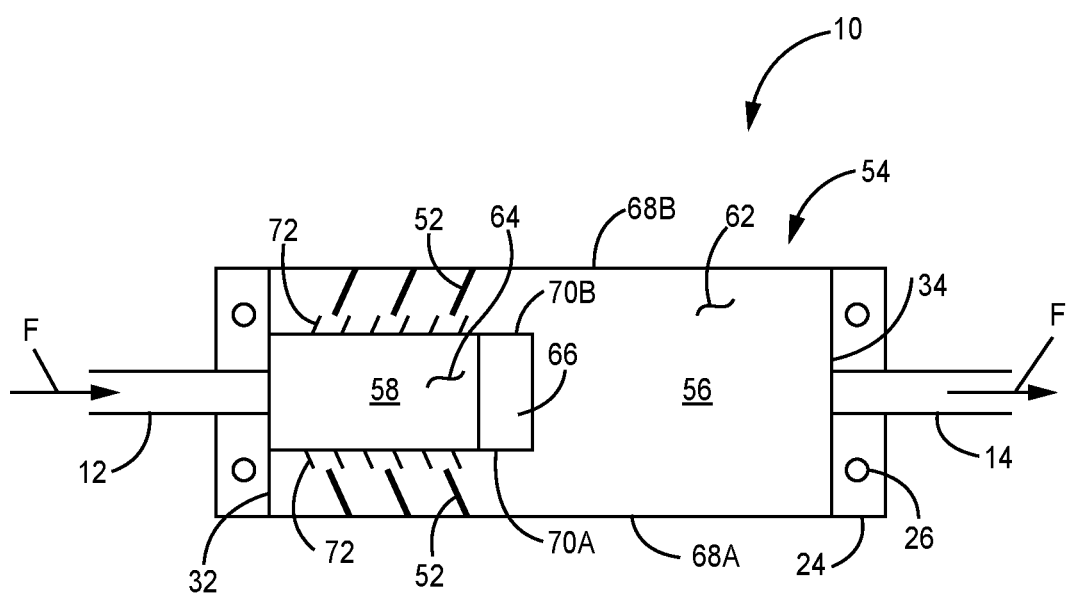
FIG. 4 is a schematic top view of the ducted smoke detector.

FIG. 2 is a schematic side view of ducted smoke detector 10. FIG. 3 is a schematic front view of ducted smoke detector 10. FIG. 4 is a schematic top view of ducted smoke detector 10. FIGS. 2-4 are discussed together. FIG. 2 shows ducted smoke detector 10, air inlet 12, air outlet 14, base plate 24, housing 54, first housing end wall 32, second housing end wall 34, smoke sensing housing portion 56, particulate separator housing portion 58, interior partition wall 60, top walls 62 and 64, transition wall 66, side walls 68A and 70A, vent louvers 72, ribs 52, particulate separator 16, smoke sensing chamber 18, electronics 74, height H1, height H2, length L1, length L2, and airflow F. FIG. 3 shows ducted smoke detector 10, air inlet 12, base plate 24, housing 54, first housing end wall 32, smoke sensing housing portion 56, particulate separator housing portion 58, interior partition wall 60, top walls 62 and 64, side walls 68A, 68B and 70A, 70B, vent louvers 72, ribs 52, mounting holes 26, particulate separator 16, smoke sensing chamber 18, electronics 74, width W1, and width W2. FIG. 4 shows ducted smoke detector 10, air inlet 12, air outlet 14, base plate 24, housing 54, first housing end wall 32, second housing end wall 34, smoke sensing housing portion 56, particulate separator housing portion 58, top walls 62 and 64, transition wall 66, side walls 68A, 68B and 70A, 70B, vent louvers 72, ribs 52, and airflow F. Reference to "top," "sides," "front," "above" and other relative location terms used herein are provided to describe the illustrated ducted smoke detector 10 and do not denote an orientation of ducted smoke detector 10 in operation. Ducted smoke detector 10 can be mounted at any orientation.

Housing 54 is disposed on base plate 24 and covers internal components of ducted smoke detector 10. Housing 54 and base plate 24 define the internal cavity of ducted smoke detector 10. Air inlet 12 extends outward from first housing end wall 32. Air outlet 14 extends outward from second housing end wall 34. Air inlet 12 and air outlet 14 are in fluid communication with the internal cavity ducted smoke detector 10. Particulate separator 16, smoke sensing chamber 18, and electronics (all shown in phantom in FIGS. 2 and 3) are disposed in the internal cavity and covered by housing 54.

Housing 54 includes smoke sensing housing portion 56 and particulate separator housing portion 58. Particulate separator housing portion 58 is disposed on smoke sensing housing portion 56 and is open to smoke sensing housing portion 56. Particulate separator housing portion 58 houses particulate separator 16. Particulate separator housing portion 58 includes vent louvers 72. Vent louvers 72 can be disposed on opposite side walls 70A. 70B. Smoke sensing housing portion 56 houses smoke sensing chamber 18 and electronics 74 (i.e., circuitry for ducted smoke detector 10).

In some embodiments, internal partition wall 60 (shown in phantom in FIGS. 2 and 3) can be provided between particulate separator 16 and base plate 24 and electronics 74. Internal partition wall 60, together with particulate separator housing portion 58, can define a cavity for particulate separator 16. Internal partition wall 60 can extend a length of particulate separator 16 such that particulate separator housing portion 58 remains open to smoke sensing housing portion 56 aft of outlet end 42 of particulate separator 16. Internal partition wall 60 is attached to internal walls of particulate separator housing portion 58 and/or smoke sensing housing portion 56. Internal partition wall 60 can be curved between side walls 68A and 70A of particulate separator housing portion 58, as shown in FIG. 3. Internal partition wall 60 can be curved toward base plate 24, such that internal partition wall 60 forms a concave cavity for particulate separator 16. Internal partition wall 60 is spaced from particulate separator 16 to allow free rotation of particulate separator 16. Internal partition wall 60 can be provided to direct particulates 50 ejected from particulate separator 16 out of the internal cavity through vent louvers 72.

Smoke sensing housing portion 56 extends from base plate 24 a first height H1 less than a total height H2 of housing 54. Smoke sensing housing portion 56 extends longitudinally between air inlet 12 and air outlet 14. Smoke sensing housing portion 56 extends a length L1 equal to a total length of housing 54. In some embodiments, smoke sensing housing portion 56 can have a length L1 of approximately 6 to 7 inches (15.24 to 17.78 cm). Smoke sensing housing portion 56 extends between side walls 68A and 68B a width W1 equal to a total width of housing 54. Smoke sensing housing portion 56 can be rectangular. Top wall 62 is disposed above smoke sensing chamber 18, electronics 74, and base plate 24. Top wall 62 can be planar. Air outlet 14 is provided through second housing end wall 34 of smoke sensing housing portion 56. Air outlet 14 can be centrally located between side walls 68A and 68B. Air outlet 14 can be located at a desired height position on second housing end wall 34 to draw airflow through smoke sensing chamber 18.

Particulate separator housing portion 58 extends outward from top wall 62 of smoke sensing housing portion 56 in a height direction. Smoke sensing housing portion 56 combined with particulate separator housing portion 58 extends from base plate 24 a height H2 equal to a total height of housing 54. In some embodiments, the total height H1 can be approximately 3 inches (7.62 cm). Particulate separator housing portion 58 extends longitudinally from first housing end wall 32 toward second housing end wall 34. Particulate separator housing portion 58 extends a length L2 that is less than the length L1 of smoke sensing housing portion 56 or total length of housing 54. The length L2 of particulate separator housing portion 58 can be selected based on the length particulate separator 16 and position of particulate separator 16 relative to smoke sensing chamber 18 as further described herein. Particulate separator housing portion 58 extends between side walls 70A and 70B a width W2 less than the total width W1 of housing 54. Particulate separator housing portion 58 is centrally located between side walls 68A and 68B of smoke sensing housing portion 56.

Particulate separator housing portion 58 has top wall 64 defining an outermost top wall of housing 54. Top wall 64 is disposed above particulate separator 16. Air inlet 12 is disposed through first housing end wall 32 of particulate separator housing portion 58. Air inlet 12 is centrally located between side walls 70A and 70B. Particulate separator housing portion 58 includes transition wall 66 disposed between side walls 70A and 70B opposite air inlet 12. Transition wall 66 extends from top wall 64 of particulate separator housing portion to top wall 62 of smoke sensing housing portion 56. Transition wall 66 is disposed aft of outlet end 42 of particulate separator 16. Transition wall 66 is angled between top wall 64 and top wall 62. Transition wall 66 slants from top wall 64 away from first housing end wall 32. Transition wall 66 is configured to direct airflow F exiting particulate separator 16 at outlet end 42 toward smoke sensing chamber 18. Preferably, outlet end 42 and housing 54 (e.g., transition wall 66) are configured to direct airflow F toward a side face of smoke sensing chamber 18.

Vent louvers 72 are provided on particulate separator housing portion 58. Vent louvers 72 provide openings through particulate separator housing portion 58. Vent louvers 72 can be slats or angled wall portions spaced along side walls 68A and 70A. Vent louvers 72 are angled to direct particulates 50 ejected from particulate separator 16 away from air inlet 12. Vent louvers 72 can be provided on side walls 70A, 70B and can extend orthogonal to base plate 24. Vent louvers 72 can extend a full or substantially full height of side walls 70A and 70B of particulate separator housing portion 58. Vent louvers 72 can be planar bodies that can be cast or co-molded with housing 54.

Ribs 52 are disposed on top wall 62 of smoke sensing housing portion 56. Ribs 52 protrude outward from top wall 62 in a height direction. Ribs 52 are disposed adjacent to vent louvers 72. Ribs 52 are spaced along side walls 70A and 70B of particulate separator housing portion 58. Ribs 52 can extend between adjacent vent louvers 72. Ribs 52 can be provided in any suitable arrangement to entrain and direct particulates 50 ejected through vent louvers 72. The number of ribs 52 can be less than the number of vent louvers 72. Ribs 52 are angled walls configured to guide particulates 50 ejected through vent louvers 72 away from air inlet 12. Ribs 52 can extend from side walls 70A and 70B of smoke sensing housing portion 56 toward edges of vent louvers 72. Ribs 52 can extend at least up to edges of vent louvers 72. Ribs 52 can extend a full or partial height of side walls 70A and 70B as suitable for entraining and directing particulates 50. Ribs 52 can be planar bodies that can be cast or co-molded with housing 54.

Housing 54 can be formed of any material suitable for containing internal components of ducted smoke detector 10. Housing 54 can be cast or molded as a unitary body or in multiple parts, which can be joined as known in the art. Generally, housing 54 includes smoke sensing housing portion 56 with top wall 62 disposed in close proximity to smoke sensing chamber 18 and particulate separator housing portion 58, extending outward from top wall 62 to provide additional space for particulate separator 16. As illustrated, particulate separator 16 can be disposed above smoke sensing chamber 18, however, other positions relative to smoke sensing chamber 18 within the internal cavity may be suitable. Vent louvers 72 are disposed adjacent to particulate separator 16 to direct particulates 50 ejected from particulate separator 16 out of ducted smoke detector 10 and away from air inlet 12. Ribs 52 can be provided to further direct particulates 50 away from air inlet 12. Housing 54 is not limited to the geometry shown. For example, housing 54 can have curved walls that more closely conform to the shape of internal components.

Figure 5:
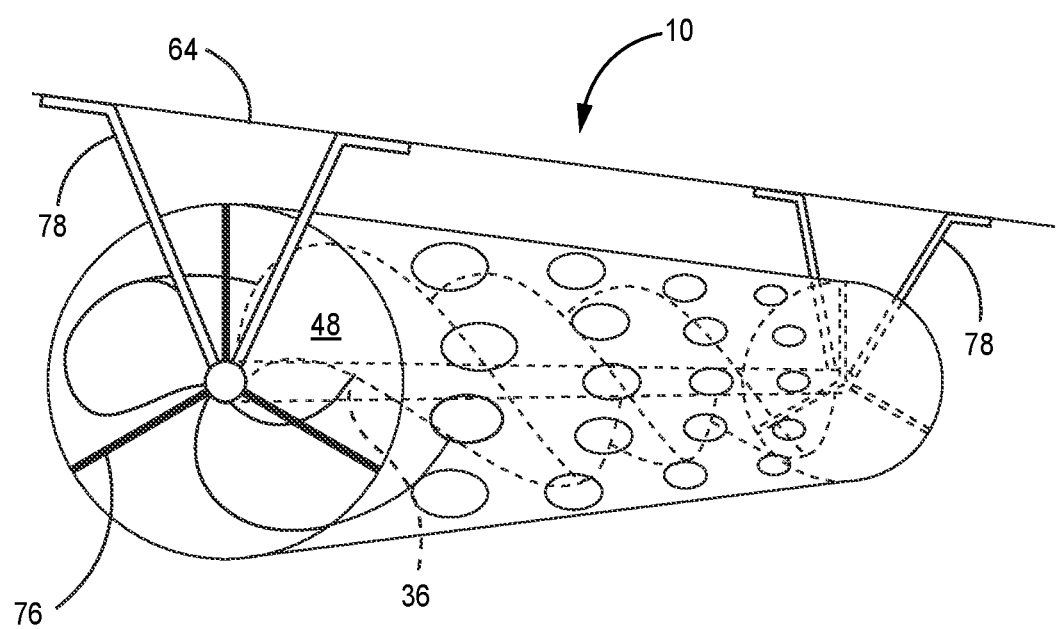
FIG. 5 is a schematic perspective view of the dust particulate separator.
Figure 6:
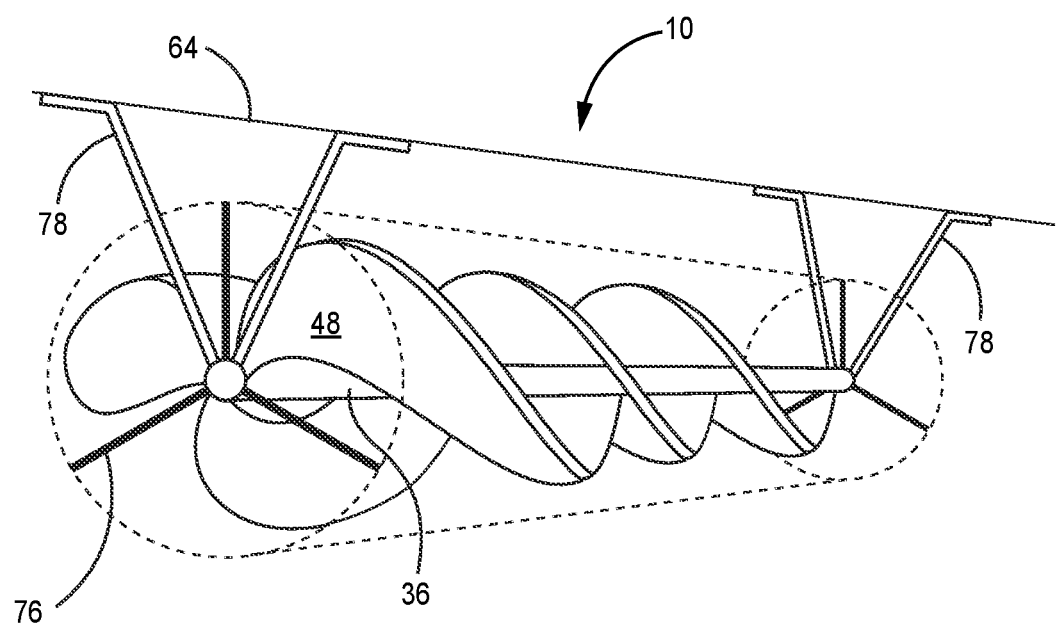
FIG. 6 is a schematic perspective view of vanes of the dust particulate separator.

FIG. 5 is a schematic perspective view of particulate separator 16. Particulate separator 16, perforated wall 38, inlet end 40, outlet end 42, holes 46, shaft 36, deflection vanes 48, mounting brackets 78, housing 54, struts 76, and airflow F are shown. FIG. 6 is a schematic perspective view of deflection vanes 48 in particulate separator 16. FIGS. 5 and 6 are discussed together herein.

Particulate separator 16 includes perforated wall 38 having holes 46 of varying size and arranged around perforated wall 38 between inlet end 40 and outlet end 42 as previously described. Particulate separator 16 has inlet end 40 and an oppositely disposed outlet end 42. Inlet end 40 and outlet end 42 are open to airflow F. Perforated wall 38 is disposed around shaft 36 and configured to rotate with shaft 36. Perforated wall 38 can be connected to shaft 36 by struts 76, which can extend from perforated wall 38 to shaft 36. Struts 76 can be provided at inlet end 40 and outlet end 42. Struts 76 are arranged to maintain a radial position of perforated wall 38 relative to deflection vanes 48 and shaft 36. Any number and arrangement of struts 76 can be provided at each of inlet end 40 and outlet end 42 as needed for structural stability. In the non-limiting example shown in FIG. 6, three struts 76 can be uniformly spaced about shaft 36 at each of inlet end 40 and outlet end 42. In some embodiments, additional struts 76 can be provided at other locations along shaft 36.

Particulate separator 16 is frustoconical in shape having a diameter that decreases from inlet end 40 to outlet end 42. Deflection vanes 48 can be configured to cause rotation of particulate separator 16 when acted on by airflow F. Deflection vanes 48 can have any shape, orientation, and arrangement suitable for driving a rotation of particulate separator 16 at a rate sufficient to force dust particulates 50 to perforated wall 38 and out holes 46 Deflection vanes 48 can have any shape, orientation, and arrangement suitable for directing particulates 50 toward perforated wall 38 and out holes 46. In some embodiments, rotation of particulate separator 16 can be motor-driven. Motor 53 (shown schematically in FIG. 1) can act as the sole driver for particulate separator 16 or as an assist if airflow F drawn through particulate separator 16 is insufficient to cause rotation of particulate separator 16 via deflection vanes 48. Deflection vanes 48 can be disposed along shaft 36 from inlet end 40 to outlet end 42 or at multiple locations on shaft 36 at and/or between inlet end 40 and outlet end 42. Deflection vanes 48 are configured to allow airflow F, including smoke particulates, to pass through particulate separator 16, while driving separation of larger/heavier dust particulates 50 from airflow F and/or directing dust particulates 50 toward perforated wall 38 and out through holes 46.

Deflection vanes 48 can capture airflow F at inlet end 40 and can drive rotation of particulate separator 16, simultaneously creating centrifugal and axial air currents, or can be configured to create centrifugal and axial air currents when driven by motor 53. The heavier particulates 50 (e.g., 1-10 micron in size) in airflow F are forced radially outward to perforated wall 38 where they can tumble before being ejected out of particulate separator 16 through holes 46 in perforated wall 38. The smaller smoke particulates (e.g., less than 1 micron in size) in airflow F travel axially through particulate separator 16 and exit through outlet end 42 to smoke sensing chamber 18. Deflection vanes 48 can be arranged to provide a flow path along shaft 36 for airflow F that is substantially devoid of dust particles 50.

Deflection vanes 48 extend a radial height or distance from shaft 36. Deflection vanes 48 can extend substantially to perforated wall 38. Deflection vanes 48 can be configured to have a near interference fit with perforated wall 38 to prevent dust particles 50 from becoming trapped between deflection vanes 48 and perforated wall 38. Deflection vanes 48 can be disposed at a desired pitch to capture airflow F and drive rotation of particulate separator 16. A smaller pitch and fewer deflection vanes 48 will typically result in a higher spin velocity while a larger and more aggressive pitch and more deflection vanes 48 will typically result in more torque and rotational force to project dust particulates 50 radially outward toward holes 46 of perforated wall 38. Preferably, deflection vanes 48 extend the full length of particulate separator 16 from inlet end 40 to outlet end 42. The pitch will determine how many vane revolutions are provided along the length of shaft 36. The height and pitch of deflection vanes 48 can be modified based on inlet airflow F velocity and expected dust particulate 50 entrainment. Deflection vanes 48 function as a means for causing rotation of perforated wall 38 and balancing the centrifugal airflow velocity and the axial airflow velocity through particulate separator 16. The configuration and arrangement of deflection vanes 48 and the size and arrangement of holes 46 through perforated wall 38 can be selected for optimized particulate separation based on system application requirements, including but not limited to available air sources, expected contamination or particulate pollution, required smoke sensitivity, false alarm immunity, and maintenance requirements. Deflection vanes 48 and perforated wall 38 can be formed of any suitable lightweight material, including but not limited to aluminum.

Shaft 36 extends outward from inlet end 40 and outlet end 42. Shaft 36 is rotatably connected to mounting brackets 78 at inlet end 40 and outlet end 42. Shaft 36 can be connected to mounting brackets 78 by a bearing (not shown) to allow shaft 36 to rotate relative to mounting brackets 78. Mounting brackets 78 connect particulate separator 16 to housing 54. Each mounting bracket 78 can be a triangular bracket that attaches to an inner surface of housing 54 in two locations. Mounting brackets 78 can be attached to an inner surface or top wall 64 (shown in FIGS. 2 and 3). Mounting brackets 78 are configured to maintain a position of particulate separator 16 in the internal cavity of ducted smoke detector 10.

The disclosed ducted particulate smoke detector is designed to prevent clogging of the smoke detector chamber and thereby improve operability and reduce maintenance requirements. The disclosed dust particulate separator can minimize or eliminate the need for unscheduled smoke detector cleaning maintenance and allow the aircraft to maintain a higher level of operational readiness.

The embodiments disclosed herein are intended to provide an explanation of the present invention and not a limitation of the invention. The present invention is not limited to the embodiments disclosed. It will be understood by one skilled in the art that various modifications and variations can be made to the invention without departing from the scope and spirit of the invention.

Any relative terms or terms of degree used herein, such as “substantially”, “essentially”, “generally”, “approximately” and the like, should be interpreted in accordance with and subject to any applicable definitions or limits expressly stated herein. In all instances, any relative terms or terms of degree used herein should be interpreted to broadly encompass any relevant disclosed embodiments as well as such ranges or variations as would be understood by a person of ordinary skill in the art in view of the entirety of the present disclosure, such as to encompass ordinary manufacturing tolerance variations, incidental alignment variations, transient alignment or shape variations induced by thermal, rotational or vibrational operational conditions, and the like. Moreover, any relative terms or terms of degree used herein should be interpreted to encompass a range that expressly includes the designated quality, characteristic, parameter or value, without variation, as if no qualifying relative term or term of degree were utilized in the given disclosure or recitation.

Discussion of Possible Embodiments

The following are non-exclusive descriptions of possible embodiments of the present invention.

A ducted smoke detector includes a housing defining an interior cavity, an air inlet in fluid communication with the interior cavity, an air outlet in fluid communication with the interior cavity, a smoke sensing chamber disposed in the interior cavity, and a particulate separator disposed between and in fluid communication with the air inlet and the smoke sensing chamber in the interior cavity. The particulate separator includes a shaft, a perforated wall disposed around the shaft, and a plurality of deflection vanes disposed on the shaft. The perforated wall extends from a first open end to a second open end, is connected to the shaft, and is configured to rotate with the shaft. The plurality of deflection vanes is disposed on the shaft and extend radially outward toward the perforated wall, the plurality of deflection vanes configured to rotate with the shaft and the perforated wall.

The ducted smoke detector of the preceding paragraph can optionally include, additionally and/or alternatively, any one or more of the following features, configurations and/or additional components:

In a further embodiment of the foregoing ducted smoke detector, the housing can include a plurality of vent louvers in fluid communication with the interior cavity, the plurality of vent louvers disposed adjacent to the perforated wall of the particulate separator.

In a further embodiment of any of the foregoing ducted smoke detectors, the housing can include a plurality of ribs disposed on an exterior surface of the housing opposite the interior cavity, the plurality of ribs disposed adjacent to the plurality of vent louvers.

In a further embodiment of any of the foregoing ducted smoke detectors, ribs of the plurality of ribs can be angled from the vent louvers away from the air inlet.

In a further embodiment of any of the foregoing ducted smoke detectors, the perforated wall can have a frustoconical shape extending between the first open end and the second open end, wherein a diameter of the first open end is greater than a diameter of the second open end.

In a further embodiment of any of the foregoing ducted smoke detectors, deflection vanes of the plurality of deflection vanes can be disposed along the length of the shaft from the first open end to the second open end.

In a further embodiment of any of the foregoing ducted smoke detectors, the perforated wall includes holes of varying size disposed between the first open end and the second open end and wherein holes disposed adjacent to the first open end are larger than holes disposed adjacent to the second open end.

In a further embodiment of any of the foregoing ducted smoke detectors, the holes of the plurality of holes can be disposed around the particulate separator.

A further embodiment of any of the foregoing ducted smoke detectors can further include a base plate connected to the housing, wherein the housing extends from the base plate to cover the interior cavity.

In a further embodiment of any of the foregoing ducted smoke detectors, the housing can include a smoke sensing housing portion extending over the smoke sensing chamber and the base plate at a first height from the base plate and a particulate separator housing portion extending over the particulate separator and base plate at a second height from the base plate with the second height being greater than the first height.

In a further embodiment of any of the foregoing ducted smoke detectors, vent louvers of the plurality of vent louvers can be disposed on the particulate separator housing portion and are angled away from the air inlet.

In a further embodiment of any of the foregoing ducted smoke detectors, the vent louvers can be disposed on opposite sides of the particulate separator housing portion.

In a further embodiment of any of the foregoing ducted smoke detectors, the smoke sensing chamber can be disposed on the base plate and wherein the particulate separator is spaced from the base plate and disposed adjacent to a wall of the particulate separator housing portion facing the base plate.

In a further embodiment of any of the foregoing ducted smoke detectors, the particulate separator housing portion can extend outward from the second open end of the particulate separator toward the air outlet and slope toward the smoke sensing chamber to join the smoke sensing housing portion.

In a further embodiment of any of the foregoing ducted smoke detectors, the housing can further include an interior partition wall disposed between the particulate separator and the base plate and connected to at least one of the particulate separator housing portion and the smoke sensing housing portion.

In a further embodiment of any of the foregoing ducted smoke detectors, the interior partition wall can have a curved surface.

In a further embodiment of any of the foregoing ducted smoke detectors, the shaft can be rotatably mounted to interior walls of the housing.

In a further embodiment of any of the foregoing ducted smoke detectors, the air inlet can be disposed in the particulate separator housing portion and the air outlet can be disposed in the smoke sensing housing portion.

In a further embodiment of any of the foregoing ducted smoke detectors, the particulate separator housing portion can extend a first length from the air inlet toward the air outlet, the first length less than a total length of the housing, and the particulate separator housing portion can extend a first width less than a total width of the housing.

In a further embodiment of any of the foregoing ducted smoke detectors, the first open end of the particulate separator can be disposed adjacent to and aligned with the air inlet.

In a further embodiment of any of the foregoing ducted smoke detectors, the plurality of deflection vanes can be configured to drive rotation of the particulate separator when acted upon by an airflow received from the air inlet.

A further embodiment of any of the foregoing ducted smoke detectors can further include a motor connected to the shaft and configured to drive rotation of the shaft.

While the invention has been described with reference to an exemplary embodiment(s), it will be understood by those skilled in the art that various changes may be made, and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment(s) disclosed, but that the invention will include all embodiments falling within the scope of the appended claims.

The invention claimed is:

1. A ducted smoke detector comprising:
   a housing defining an interior cavity;
   an air inlet in fluid communication with the interior cavity;
   an air outlet in fluid communication with the interior cavity;
   a smoke sensing chamber disposed in the interior cavity; and
   a particulate separator disposed between and in fluid communication with the air inlet and the smoke sensing chamber in the interior cavity, the particulate separator comprising:
   a shaft;
   a perforated wall disposed around the shaft and extending from a first open end to a second open end, the perforated wall connected to the shaft and configured to rotate with the shaft; and
   a plurality of deflection vanes disposed on the shaft and extending radially outward toward the perforated wall, the plurality of deflection vanes configured to rotate with the shaft and the perforated wall.

2. The ducted smoke detector of claim 1, wherein the housing comprises a plurality of vent louvers in fluid communication with the interior cavity, the plurality of vent louvers disposed adjacent to the perforated wall of the particulate separator.

3. The ducted smoke detector of claim 2, wherein the housing comprises a plurality of ribs disposed on an exterior surface of the housing opposite the interior cavity, the plurality of ribs disposed adjacent to the plurality of vent louvers.

4. The ducted smoke detector of claim 3, wherein ribs of the plurality of ribs are angled from the vent louvers away from the air inlet.

5. The ducted smoke detector of claim 2, wherein the perforated wall has a frustoconical shape extending between the first open end and the second open end, wherein a diameter of the first open end is greater than a diameter of the second open end.

6. The ducted smoke detector of claim 5, wherein deflection vanes of the plurality of deflection vanes are disposed along a length of the shaft from the first open end to the second open end.

7. The ducted smoke detector of claim 5, wherein the perforated wall comprises holes of varying size disposed between the first open end and the second open end, wherein holes disposed adjacent to the first open end are larger than holes disposed adjacent to the second open end.

8. The ducted smoke detector of claim 2, and further comprising a base plate connected to the housing, wherein the housing extends from the base plate to cover the interior cavity.

9. The ducted smoke detector of claim 8, wherein the housing comprises:
   a smoke sensing housing portion extending over the smoke sensing chamber and the base plate at a first height from the base plate; and
   a particulate separator housing portion extending over the particulate separator and base plate at a second height from the base plate, wherein the second height is greater than the first height.

10. The ducted smoke detector of claim 9, wherein vent louvers of the plurality of vent louvers are disposed on the particulate separator housing portion and are angled away from the air inlet.

11. The ducted smoke detector of claim 10, wherein the vent louvers are disposed on opposite sides of the particulate separator housing portion.

12. The ducted smoke detector of claim 9, wherein the smoke sensing chamber is disposed on the base plate and wherein the particulate separator is spaced from the base plate and disposed adjacent to a wall of the particulate separator housing portion facing the base plate.

13. The ducted smoke detector of claim 12, wherein the particulate separator housing portion extends outward from the second open end of the particulate separator toward the air outlet and slopes toward the smoke sensing chamber to join the smoke sensing housing portion.

14. The ducted smoke detector of claim 12, wherein the housing further comprises an interior partition wall disposed between the particulate separator and the base plate and connected to at least one of the particulate separator housing portion and the smoke sensing housing portion.

15. The ducted smoke detector of claim 14, wherein the interior partition wall has a curved surface.

16. The ducted smoke detector of claim 9, wherein the shaft is rotatably mounted to interior walls of the housing.

17. The ducted smoke detector of claim 9, wherein the air inlet is disposed in the particulate separator housing portion and wherein the air outlet is disposed in the smoke sensing housing portion.

18. The ducted smoke detector of claim 9, wherein the particulate separator housing portion extends a first length from the air inlet toward the air outlet, the first length less than a total length of the housing, and wherein the particulate separator housing portion extends a first width less than a total width of the housing.

19. The ducted smoke detector of claim 2, wherein the first open end of the particulate separator is disposed adjacent to and aligned with the air inlet.

20. The ducted smoke detector of claim 1, wherein the plurality of deflection vanes is configured to drive rotation of the particulate separator when acted upon by an airflow received from the air inlet.

* * * * *